United States Patent [19]

Cheshire et al.

[11] Patent Number: 6,028,074
[45] Date of Patent: Feb. 22, 2000

[54] PYRAZOLO[3,4-D]PYRIMIDINEONE COMPOUNDS

[75] Inventors: David Cheshire; Martin Cooper; David Donald; Philip Thorne, all of Loughborough, United Kingdom

[73] Assignee: Astra Pharmaceuticals, Ltd., London, United Kingdom

[21] Appl. No.: 09/068,304

[22] PCT Filed: Aug. 7, 1998

[86] PCT No.: PCT/SE98/00640

§ 371 Date: May 7, 1998

§ 102(e) Date: May 7, 1998

[87] PCT Pub. No.: WO98/46606

PCT Pub. Date: Oct. 22, 1998

[30] Foreign Application Priority Data

Apr. 15, 1997 [SE] Sweden .................................. 9701398

[51] Int. Cl.[7] ...................... A61K 31/505; C07D 487/04
[52] U.S. Cl. ............................................ 514/258; 544/262
[58] Field of Search .............................. 544/262; 514/258

[56] References Cited

U.S. PATENT DOCUMENTS 4,824,848  4/1989  Naka et al. .............................. 544/262

FOREIGN PATENT DOCUMENTS 0 063 381  10/1982  European Pat. Off. .
0 166 054  1/1986  European Pat. Off. .
94 13643  6/1994  WIPO .

OTHER PUBLICATIONS

Michne et al. Novel inhibitors of the Nuclear Factor of . . . J. Med. Chem. 38, 2557–2569, 1995.

*Primary Examiner*—Richard L. Raymond
*Assistant Examiner*—V. Balasubramanian
*Attorney, Agent, or Firm*—Nixon & Vanderhye

[57] ABSTRACT

The invention relates to pharmaceutically useful pyrazolo [3,4-d]pyrimidinedione compounds, processes for their production, pharmaceutical compositions containing them and their use for the treatment of various diseases.

12 Claims, No Drawings

PYRAZOLO[3,4-D]PYRIMIDINEONE COMPOUNDS

This application is a 371 of PCT/SE98/00640, filed Apr. 7, 1998.

The present invention relates to pharmaceutically useful pyrazolo[3,4-d]pyrimidinedione compounds, processes for their production, pharmaceutical compositions containing them and their use for the treatment of various diseases.

T-cells play an important role in the immune response, however in autoimmune disease T-cells are activated against particular tissues, e.g. causing the inflammation associated with rheumatoid arthritis. Interleukin-2 (IL-2) is an essential autocrine growth factor for T-cells and hence inhibition of IL-2 transcription is beneficial in the modulation of autoimmune disease. Formation of a transcriptional complex of the protein nuclear factor of activated T-cells-1 (NFAT-1) on the EL-2 promoter is essential for IL-2 transcription. NFAT-1 mediated transcription has therefore been proposed as appropriate molecular target for immunomodulation, Y. Baine et al., *J. Immunol.*, 1995, 154, 3667–3677. W. F. Michne et al., in *J. Med. Chem.* (1995) 38, 2557–2569 disclose a number of quinazoline-2,4-diones and pyrrolo[3,4-d]pyrimidine-2,4-diones which inhibit transcription regulated by the DNA region bound by the NFAT-1 protein.

According to the invention there is provided a compound of formula (I):

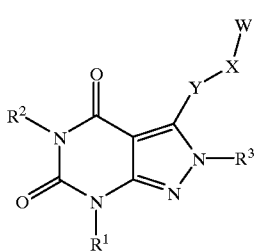

in which:

$R^1$ is $C_{1-6}$alkyl, $C_{3-6}$alkenyl or $C_{3-6}$cycloalkyl;
$R^2$ is $C_{1-4}$alkyl or $C_{3-6}$alkenyl;
$R^3$ is 1- or 2-indanyl, 1- or 2-(1,2,3,4-tetrahydronaphthalenyl), 9-fluorenyl, acenaphthyl or $CHR^4(CH_2)_nAr$ where n is 0 or 1, $R^4$ is hydrogen or $C_{1-6}$alkyl and Ar is quinolinyl, naphthalenyl, benzodioxolinyl optionally susbstituted by one or more halogen atoms, or phenyl optionally substituted by one or more substituent groups selected from halogen, $C_{1-6}$alkyl, $C_{1-6}$alkoxy and phenylsulfonylmethyl;
W is H, $CH_2OH$, $CO_2H$, $CO_2C_{1-6}$alkyl, $CH_2NR^5R^6$, $CONR^5R^6$, where $R^5$ and $R^6$ are independently hydrogen or $C_{1-6}$alkyl, or together with the nitrogen atom to which they are attached form a 3- to 8-membered heterocyclic ring optionally further containing an oxygen atom or a group $NR^7$ where $R^7$ is hydrogen or $C_{1-6}$alkyl, or W is pyridyl or phenyl, each of which may be optionally substituted by one or more substituent groups selected from halogen, hydroxyl, $C_{1-6}$alkyl and $C_{1-6}$alkoxy; X is a bond or $C_{_5}$alkylene;
Y is $S(O)_p$, $C\equiv C$, $CH=CH$, $CH_2CH_2$ or $CH_2CH=CH$; and
p is 0, 1 or 2;
or a pharmaceutically acceptable salt thereof, provided that:
X is not a bond when W is H, $CH_2OH$, $CO_2H$, $CO_2C_{1-6}$alkyl, $CH_2NR^5R^6$ or $CONR^5R^6$ and Y is sulfur.

Alkyl and alkenyl groups whether alone or as part of another group, may be linear or branched. As defined herein alkenyl groups are those where the double bond is not adjacent to a heteroatom.

Suitably $R^1$ is $C_{1-6}$alkyl, $C_{3-6}$alkenyl or $C_{3-6}$cycloalkyl. Preferably $R^1$ is a $C_{1-4}$alkyl or $C_{3-4}$alkenyl group such as methyl, ethyl, propyl, butyl, 2-methyl-1-propyl, propenyl, butenyl or 2-methyl-2-propenyl.

Suitably $R^2$ is $C_{1-4}$alkyl (e.g. methyl, ethyl, propyl, butyl or 2-methyl-1-propyl) or $C_{3-6}$alkenyl (e.g. propenyl, butenyl, pentenyl, hexenyl or 2-methyl-2-propenyl). Preferably $R^2$ is $C_{1-4}$alkyl, most preferably methyl.

Suitably $R^3$ is 1- or 2-indanyl, 1- or 2-(1,2,3,4-tetrahydronaphthalenyl), 9-fluorenyl, acenaphthyl or $CHR^4(CH_2)_nAr$ where n is 0 or 1, $R^4$ is hydrogen or $C_{1-6}$alkyl (e.g. methyl, ethyl, propyl, butyl, pentyl or hexyl) and Ar is quinolinyl, naphthalenyl, benzodioxolinyl optionally susbstituted by one or more, e.g. one, two or three, halogen atoms (e.g. fluorine, chlorine or bromine), or phenyl optionally substituted by one or more, e.g. one to four, preferably one or two, substituent groups selected from halogen (e.g. fluorine, chlorine or bromine), $C_{1-6}$alkyl (e.g. methyl, ethyl, propyl, butyl, pentyl or hexyl), $C_{1-6}$alkoxy (e.g. methoxy, ethoxy, propoxy or butoxy) and phenylsulfonylmethyl.

Preferably $R^3$ is $CHR^4(CH_2)_nAr$ where n is 0, $R^4$ is hydrogen and Ar is quinolinyl, naphthalenyl, benzodioxolinyl substituted by one or more halogen atoms, or phenyl substituted by one or more substituent groups selected from halogen atoms and phenylsulfonylmethyl.

Suitably W is H, $CH_2OH$, $CO_2H$, $CO_2C_{1-6}$alkyl, preferably $CO_2C_{1-4}$alkyl (e.g. $CO_2CH_3$, $CO_2C_2H_5$, $CO_2C_3H_7$ or $CO_2C_4H_9$), $CH_2NR^5R^6$, $CONR^5R^6$, where $R^5$ and $R^6$ are independently hydrogen or $C_{1-6}$alkyl (e.g. methyl, ethyl, propyl, butyl, pentyl or hexyl), or together with the nitrogen atom to which they are attached form a 3- to 8-membered heterocyclic ring optionally further containing an oxygen atom or a group $NR^7$ where $R^7$ is hydrogen or $C_{1-6}$alkyl (e.g. methyl, ethyl, propyl, butyl, pentyl or hexyl), or W is pyridyl or phenyl, each of which may be optionally substituted by one or more, e.g. one, two or three, substituent groups selected from halogen (e.g. fluorine, chlorine or bromine), hydroxyl, $C_{1-6}$alkyl (e.g. methyl, ethyl, propyl, butyl, pentyl or hexyl) and $C_{1-6}$alkoxy (e.g. methoxy, ethoxy, propoxy or butoxy).

Examples of groups where $R^5$ and $R^6$ form a 3- to 8-membered heterocyclic ring include piperidine, morpholine and piperazine rings.

Preferably W is H, $CH_2OH$, $CO_2H$, $CO_2C_{1-6}$alkyl or pyridyl.

Suitably X is a bond or $C_{1-5}$alkylene, preferably $C_{1-3}$alkylene.

Suitably Y is $S(O)_p$ where p is 0, 1 or 2, $C\equiv C$, $CH=CH$, $CH_2CH_2$ or $CH_2CH=CH$. Preferably Y is sulfur or $CH_2CH_2$.

A preferred subset of compounds of formula (I) is one in which $R^1$ is $C_{1-4}$alkyl or $C_{3-4}$alkenyl; $R^2$ is $C_{1-4}$alkyl; $R^3$ is $CHR^4(CH_2)_nAr$ where n is 0 or 1, $R^4$ is hydrogen or $C_{1-6}$alkyl and Ar is quinolinyl, naphthalenyl, benzodioxolinyl optionally susbstituted by one or more halogen atoms, or phenyl optionally substituted by one or more substituent groups selected from halogen, $C_{1-6}$alkyl, $C_{1-6}$alkoxy and phenylsulfonylmethyl; W is H, $CH_2OH$, $CO_2H$, $CO_2C_{1-6}$alkyl or pyridyl; X is a bond or $C_{1-3}$alkylene; and Y is sulfur or $CH_2CH_2$, provided that:
X is not a bond when W is H, $CH_2OH$, $CO_2H$ or $CO_2C_{1-6}$alkyl and Y is sulfur.

An especially preferred subset of compounds of formula (I) is one in which $R^1$ is $C_4$alkyl or $C_4$alkenyl; $R^2$ is methyl; $R^3$ is $CHR^4(CH_2)_nAr$ where n is 0, $R^4$ is hydrogen and Ar is quinolinyl, naphthalenyl, benzodioxolinyl optionally susbstituted by one or more chlorine atoms, or phenyl optionally substituted by one or more substituent groups selected from halogen and phenylsulfonylmethyl; W is H, $CH_2OH$, $CO_2H$, $CO_2CH_3$ or 2-pyridyl; X is a bond or $C_{1-3}$alkylene; Y is sulfur or $CH_2CH_2$, provided that:

X is not a bond when W is H, $CH_2OH$, $CO_2H$ or $CO_2CH_3$ and Y is sulfur.

Particularly preferred compounds of the invention include:

3-[(3-Hydroxypropyl)thio]-5-methyl-7-(2-methyl-2-propenyl)-2-(1-naphthalenylmethyl)-2H-pyrazolo[3,4-d]pyrimidine-4,6[5H,7H]-dione, 5-Methyl-7-(2-methyl-2-propenyl)-2-(1-naphthalenylmethyl)-3-[(2-pyridinyl)thio]-2H-pyrazolo[3,4-d]pyrimidine-4,6[5H,7H]-dione, 3-[(2-Hydroxyethyl)thio)-5-methyl-7-(2-methyl-2-propenyl)-2-(1-naphthalenylmethyl-2H-pyrazolo[3,4-d]pyrimidine-4,6[5H,7H]-dione, 3-(4-Hydroxybutyl)-5-methyl-7-(2-methylpropyl)-2-(1-naphthalenylmethyl)-2H-pyrazolo[3,4-d]pyrimidine-4,6(5H,7H)-dione, 5-Methyl-7-(2-methylpropyl)-2-(1-naphthalenylmethyl)-3-propylthio-2H-pyrazolo[3,4-d]pyrimidine-4,6(5H,7H)-dione, 3-[(3-Hydroxypropylthio]-5-methyl-7-(2-methylpropyl)-2-(1-naphthalenylmethyl)-2H-pyrazolo[3,4-d]pyrimidine-4,6(5H,7H)-dione, Methyl 4-[(4,5,6,7-tetrahydro-5-methyl-7-{2-methylpropyl}-2-{1-naphthalenylmethyl}-4,6-dioxo-2H-pyrazolo[3,4-d]pyrimidin-3-ylthio]butanoic acid, 4-[(4,5,6,7-tetrahydro-5-methyl-7-{2-methylpropyl}-2-{1-naphthalenylmethyl}-4,6-dioxo-2H-pyrazolo[3,4-d]pyrimidin-3-yl)thio]butanoic acid, 3-[(3-Hydroxypropyl)thio]-5-methyl-7-(2-methylpropyl)-2-(2-{phenylsulfonylmethyl}phenylmethyl)-2H-pyrazolo[3,4-d]pyrimidine-4,6(5H,7H)-dione, 2-({5-Chlorobenzo[1,3]dioxol-6-yl}methyl)-3-[(3-hydroxypropylthio] -5-methyl-7-(2-methylpropyl)-2H-pyrazolo[3,4-d]pyrimidine-4,6(5H,7H)-dione, 2-(3-Chloro-2-fluorophenylmethyl)-3-[(3-hydroxypropyl)thio]-5-methyl-7-(2-methylpropyl)-2H-pyrazolo[3,4-d]pyrimidine-4,6(5H,7H)-dione, and 3-[(3-Hydroxypropyl)thio]-5-methyl-7-(2-methylpropyl)-2-(2-quinolinylmethyl)-2H-pyrazolo[3,4-d]pyrimidine-4,6(5H,7H)-dione, and pharmaceutically acceptable salts thereof.

Compounds of the invention can form pharmaceutically acceptable salts. The compounds of the formula (I) can form acid addition salts with acids, such as conventional pharmaceutically acceptable acids, for example, maleic, hydrochloric, hydrobromic, phosphoric, acetic, fumaric, salicylic, citric, lactic, oxalic, mandelic, tartaric and methanesulfonic acids.

Certain compounds of formula (I) are capable of existing in stereoisomeric forms including enantiomers and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

According to a further aspect of the invention there is also provided a process for the preparation of a compound of formula (I) which comprises:

(a) reaction of a compound of formula (II):

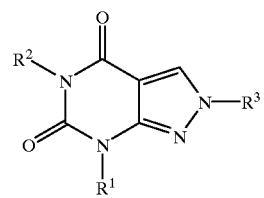

(II)

in which $R^1$, $R^2$ and $R^3$ are as defined in formula (I) with a compound of formula (III):

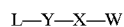

L—Y—X—W (III)

in which L is a leaving group, Y is sulphur, and X and W are as defined in formula (I), or (b) when Y is $CH_2CH_2$ or $CH_2CH=CH$ and $R^3$ is $CHR^4(CH_2)_n Ar$, reaction of a compound of formula (IV):

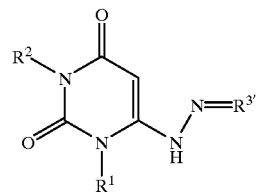

(IV)

in which $R^{3'}$ is a precursor to the $R^3$ group $CHR^4(CH_2)_n Ar$ and $R^1$ and $R^2$ are as defined in formula (I), with a compound of formula (V):

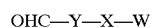

OHC—Y—X—W (V)

in which Y is $CH_2CH_2$ or $CH_2CH=CH$ and W and X are as defined in formula (I), or p0 (c) when Y is C≡C, CH=CH or $CH_2CH=CH$, reacting a compound of formula (VI):

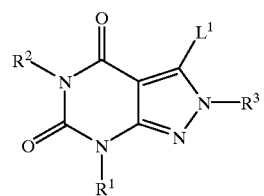

(VI)

in which $L^1$ represents a leaving group and $R^1$, $R^2$ and $R^3$ are as defined in formula (I) with a compound of formula (VII) or (VIII):

$H_2C=CH—X^a W$ (VII)

HC≡C—XW (VIII)

wherein, in formula (VII), $X^a$ is a bond or $C_{1-6}$alkylene and W is as defined in formula (I), and wherein, in formula (VIII), W and X are as defined in formula (I), and optionally thereafter:

converting the compound of formula (I) to a further compound of formula (I), and/or forming a pharmaceutically acceptable salt.

The reaction of compounds of formulae (II) and (III) is typically carried out by treating the compound of formula (II) with a suitable base in an inert solvent at reduced temperature. Suitable bases include lithium diisopropylamide (LDA) in tetrahydrofuran (THF) at or below −40° C. Preferred leaving groups L include sulfinate, tosyl or tolylsulfinyl. Alternatively when Y is sulfur, the leaving group itself may be a group of formula Y—X—W such that the compound of formula (III) is a dimer of formula W—X—S—S—X—W.

Compounds of formulae (IV) and (V) are suitably reacted in an inert solvent such as dimethylformamide (DMF) at elevated temperature, for example at reflux. The group $R^{3'}$ is a suitable precursor to $R^3$ in compounds of formula (I) such that $R^{3'}$ is an alkylidine precursor to $R^3$.

Compounds of formula (I) in which Y represents sulphur can be converted to further compounds of formula (I) in which Y represents SO or $SO_2$ by an oxidation reaction using, for example, as oxidising agent 3-chloroperoxybenzoic acid or potassium peroxymonosulphate (commercially sold under the trade mark "OXONE").

Compounds of formula (II) can be prepared by reaction of a compound of formula (IX):

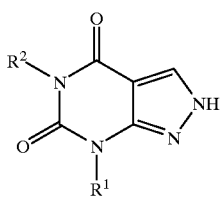

(IX)

in which $R^1$ and $R^2$ are as defined in formula (I) with a compound of formula (X):

$L^2$—$R^3$ (X)

in which $L^2$ is a leaving group and $R^3$ is as defined in formula (I).

Reaction of compounds of formula (IX) and (X) is suitably carried out in the presence of a base such as sodium or potassium carbonate in a suitable solvent such as acetone. Suitable leaving groups $L^2$ include halogen.

Compounds of formula (IX) can be prepared by reaction of a compound of formula (XI):

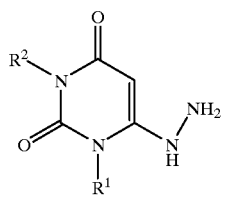

(XI)

in which $R^1$ and $R^2$ are as defined in formula (I) with dimethylformamide dimethylacetal at elevated temperature, for example at about 90° C. or with phosphorus oxychloride ($POCl_3$) in dimethylformamide (DMF) at about 0° C.

Compounds of formula (XI) can be prepared using standard procedures known in the art, for example, by treating the corresponding halide with hydrazine hydrate.

Compounds of formula (IV) can be prepared by reacting a compound of formula (XI) as defined above with a compound of formula (XII):

$Ar(CH_2)_n$—$CR^4$=O (XII)

in which Ar, n and $R^4$ are as defined in formula (I).

Reaction of compounds of formula (VI) and (VII) can be carried out in the presence of $Pd(OAc)_2/P(0/-Tol)_3$ in the presence of a base such as triethylamine in a suitable solvent such as acetonitrile. A mixture of compounds of formula (I) are obtained where X' is X as defined in formula (I) minus one carbon atom:

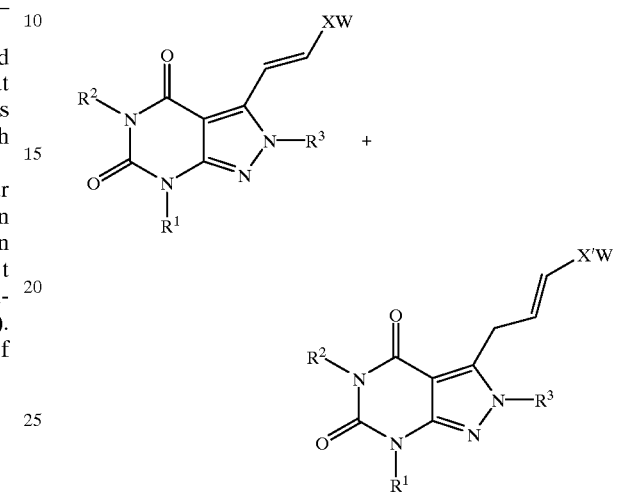

Compounds of formula (VI) and (VIII) can be reacted in the presence of a palladium catalyst with copper iodide in the presence of a base such as triethylamine in a suitable solvent such as acetonitrile. Preferred catalysts include $Pd(Ph_3P)_2Cl_2$.

Compounds of formula (VI) can be prepared by reacting a compound of formula (XIII):

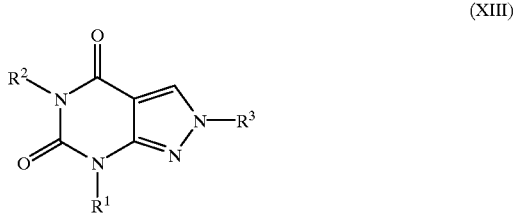

(XIII)

in which $R^1$, $R^2$ and $R^3$ are as defined in formula (I), with a base followed by a halogen (e.g. iodine) to become the group $L^1$. A compound of formula (XIII) can be treated with an organic base such as lithium diisopropylamide (LDA) in an inert solvent such as tetrahydrofuran (THF) at reduced temperature, for example at about −70° C. Iodine is then added and the reaction mixture allowed to warm to ambient temperature.

Compounds of formula (I) can be converted to further compounds of formula (I) using procedures known in the art. For example the reaction products of process (c) can be hydrogenated to give compounds of formula (I) where X/Y form an alkylene chain. Alternatively compounds of formula (I) where Y is C≡C can be hydrogenated using a lindlar catalyst to the corresponding compounds of formula (I) where Y is C=C.

The group W can also be interconverted, for example when W is $CO_2H$, compounds of formula (I) can be converted to compounds of formula (I) where W is $CO_2C_{1-6}$alkyl, $CONR^5R^6$ or $CH_2NR^5R^6$. When W is $CH_2OH$ compounds of formula (I) can be converted to compounds of formula (I) where W is $CH_2NR^5R^6$. Suitable procedures for these conversions are shown in the scheme below:

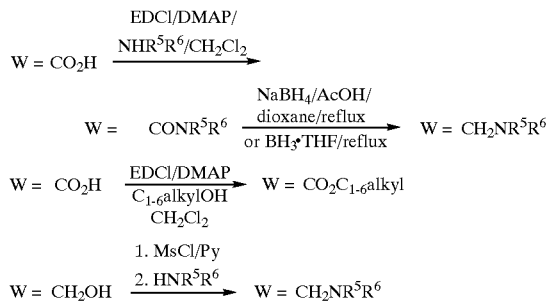

Compounds of formulae (IE), (V), (VII), (VIII), (X) and (XII) are either commercially available, are well known in the literature or may be prepared easily using known techniques.

Novel intermediate compounds form a further aspect of the invention.

It will be appreciated by those skilled in the art that in the process steps described above the functional groups of intermediate compounds may need to be protected by protecting groups. The protection of functional groups may take place before any of the process steps hereinbefore described. Protecting groups may be removed following a reaction step or at the end of the reaction process using techniques which are well known to those skilled in the art. The use of protecting groups is fully described in "Protective Groups in Organic Chemistry", edited by J W F McOmie, Plenum Press (1973), and "Protective Groups in Organic Synthesis", 2nd edition, T W Greene & P G M Wuts, Wiley-Interscience (1991).

Salts of the compounds of formula (I) may be formed by reacting the free acid, or a salt thereof, or the free base, or a salt thereof, with one or more equivalents of the appropriate base or acid. The reaction may be carried out in a solvent or medium in which the salt is insoluble or in a solvent in which the salt is soluble, e.g. ethanol, tetrahydrofuran or diethyl ether, which may be removed in vacuo, or by freeze drying. The reaction may also be a metathetical process or it may be carried out on an ion exchange resin. The non-toxic physiologically acceptable salts are preferred, although other salts may be useful, e.g. in isolating or purifying the product.

The compounds of the present invention are advantageous in that they possess pharmacological activity. They are therefore indicated as pharmaceuticals for use in the (prophylactic) treatment of autoimmune, inflammatory, proliferative and hyperproliferative diseases and immunologically-mediated diseases including rejection of transplanted organs or tissues and Acquired Immunodeficiency Syndrome (AIDS). Examples of these conditions are:

(1) (the respiratory tract) reversible obstructive airways diseases including asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) (bone and joints) rheumatoid arthritis, seronegative spondyloarthropathies (including ankylosing spondylitis, psoriatic arthritis and Reiter's disease), Behcet's disease, Sjogren's syndrome and systemic sclerosis;

(3) (skin) psoriasis, atopical dermatitis, contact dermatitis and other eczmatous dermitides, seborrhoetic dermitis, Lichen planus, Pemphigus, bullous Pemphigus, Epidermolysis bullosa, urticaria, angiodermas, vasculitides, erythemas, cutaneous eosinophilias, uveitis, Alopecia areata and vernal conjunctivitis;

(4) (gastrointestinal tract) Coeliac disease, proctitis, eosinopilic gastro-enteritis, mastocytosis, Crohn's disease, ulcerative colitis, food-related allergies which have effects remote from the gut, e.g., migraine, rhinitis and eczema;

(5) (other tissues and systemic disease) multiple sclerosis, atherosclerosis, Acquired Immunodeficiency Syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia pupura;

(6) (allograft rejection) acute and chronic following for example transplantation of kidney, heart, liver, lung, bone marrow, skin and cornea; and chronic graft versus host disease.

The compounds of the invention are also indicated for use as antimicrobial agents, and thus may be used in the treatment of diseases caused by pathogenic micro-organisms.

Accordingly, the present invention provides a compound of formula (I), or a pharmaceutically acceptable salt thereof, as hereinbefore defined for use in therapy.

In another aspect, the invention provides the use of a compound of formula (I), or a pharmaceutically acceptable salt thereof, as hereinbefore defined in the manufacture of a medicament for use in therapy.

In particular, the present invention provides the use of a compound of formula (I), or a pharmaceutically acceptable salt thereof, as hereinbefore defined in the manufacture of an immunosuppressive pharmaceutical composition. The compounds of the invention can also be administered in combination with other immunosuppressants known in the art such as FK506 and Cyclosporin.

According to a further aspect of the invention there is provided the use of a compound of formula (I), as hereinbefore defined, or a pharmaceutically acceptable salt thereof, in the manufacture of a medicament for the treatment of a reversible obstructive airways disease.

For the above-mentioned therapeutic uses the dosage administered will, of course, vary with the compound employed, the mode of administration, the treatment desired and the disease indicated.

According to the invention there is further provided a pharmaceutical composition comprising preferably from 0.05 to 99% w (per cent by weight), e.g. less than 80% w, and more preferably from 0.1 to 70% w, e.g. less than 50% w, of a compound of formula (I), or a pharmaceutically acceptable salt thereof, as defined above in combination with a pharmaceutically acceptable diluent or carrier.

The invention further provides a process for the preparation of a pharmaceutical composition of the invention which comprises mixing a compound of formula (I), or a pharmaceutically-acceptable salt thereof, as hereinbefore defined with a pharmaceutically acceptable diluent or carrier.

The pharmaceutical composition of the invention may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally.

According to a further aspect of the invention, there is provided a method of effecting immunosuppression which comprises administering to a patient a therapeutically effective amount of a compound of formula (I), or a pharmaceutically acceptable salt thereof, as defined above.

The invention is illustrated by the following examples.

EXAMPLE 1

3-[(3-Hydroxypropyl)thio]-5-methyl-7-(2-methyl-2-propenyl)-2-(1-naphthalenylmethyl)-2H-pyrazolo[3,4-d]pyrimidine-4,6[5H,7H]-dione

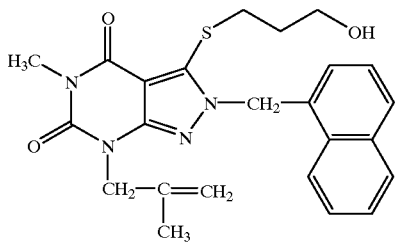

(a) 1-Methylbarbituric acid

Acetic anhydride (17 ml) was added to a solution of malonic acid (10 g) and methylurea (6.25 g) in acetic acid (23 ml) at 65° C. The mixture was heated to 90–95° C. for 3 hours then cooled to room temperature. The resulting solution was concentrated under reduced pressure and the residue was redissolved in ethanol (50 ml). Ether (5 ml) was added and the mixture was allowed to stand for 16 hours at room temperature before being chilled for 4 hours at 4° C. The precipitated solid was filtered and washed with ether. The solid was redissolved in warm water (50 ml) and the solution concentrated under reduced pressure until solid started to precipitate. The mixture was cooled to room temperature and the solid that formed was collected and dried in vacuo to give the sub-title compound (3.34 g) as a solid.

Melting point: 130–131° C. MS (EI) 142 (M$^+$) $^1$H NMR (DMSO-d$_6$) δ 3.05 (3H, s); 3.58 (2H, s); 11.33 (1H, s, br).

(b) 6-Chloro-3-methylpyrimidine-2,4[1H,3H]-dione

1-Methylbarbituric acid (10 g) was suspended in phosphorus oxychloride (70 ml). Water (2 ml) was added and the mixture was heated at reflux for 40 minutes. The reaction was allowed to cool and was then concentrated under reduced pressure. The residue was poured onto a mixture of ice and water (200 ml). When the ice had melted, the precipitated solid was collected, washed with water and dried in vacuo at 50° C. to give the sub-title compound (6.86 g) as a yellow solid.

MS (EI) 160/162 (M$^+$) $^1$H NMR (CDCl$_3$/DMSO-d$_6$) δ 3.24 (3H, s); 5.74 (1H, s); 12.18 (1H, s, br).

(c) 6-Hydrazino-3-methyl-1-(2-methyl-2-propenyl)pyrimidine-2,4[1H,3H]-dione

3-Bromo-2-methylpropene (1.65 ml) and potassium carbonate (4.00 g) were added to a solution of 6-chloro-3-methylpyrimidine-2,4[1H,3H]-dione (2.00 g) in acetone (50 ml). The mixture was heated at reflux for 24 hours and then cooled to room temperature. The solution was filtered and the solid was washed with acetone (2×25 ml). The combined filtrate was concentrated under reduced pressure to give a yellow solid (1.25 g). This was redissolved in ethanol (15 ml) and hydrazine hydrate (5 ml) was added. The mixture was heated at reflux for 15 minutes, allowed to cool to room temperature, and then evaporated under reduced pressure. The residue was coevaporated with ethanol (2×20 ml) under reduced pressure and was then recrystallised from ethanol to give the subtitle compound (0.75 g).

Melting point: 186×188° C. MS (EI) 210 (M$^+$) $^1$H NMR (DMSO-d$_6$) δ 1.70 (3H, s); 3.10 (3H, s); 4.36 (4H, s, br); 4.44 (1H, s); 4.74 (1H, s); 5.12 (1H, s); 7.88 (1H, s, br).

(d) 5-Methyl-7-(2-methyl-2-propenyl)-2H-pyrazolo[3,4-d]pyrimidine-4,6-[5H,7H]-dione A mixture of 6-hydrazino-3-methyl-1-(2-methyl-2-propenyl)pyrimidine-2,4[1H,3H]-dione (0.575 g) and dimethylformamide dimethylacetal (0.73 ml) was heated at 90° C. for 20 minutes. The mixture was allowed to cool and was directly purified by column chromatography over silica eluting with ethyl acetate: hexane (2:1) and then recrystallisation from ethyl acetate/hexane to give the subtitle compound (0.063 g). Melting point: 232–233° C. MS (EI) 220 (M$^+$) $^1$H NMR (CDCl$_3$/DMSO-d$_6$) δ 1.80 (3H, s); 3.39 (3H, s); 4.60 (2H, s); 4.75 (1H, s), 4.89 (1H, s); 8.04 (1H, s); 13.04 (1H, s, br).

(e) 5-Methyl-7-(2-methyl-2-propenyl)-2-(1-naphthalenylmethyl)-2H-pyrazolo-[3,4-d]pyrimidine-4,6[5H,7H]-dione 1-(Chloromethyl)naphthalene (0.214 ml) and potassium carbonate (0.60 g) were added to a suspension of 5-methyl-7-(2-methyl-2-propenyl)-2H-pyrazolo[3,4-d]pyrimidine-4,6[5H,7H]-dione (0.215 g) in acetone (10 ml). The mixture was stirred at room temperature for 16 hours and then heated at reflux for 2 hours. The mixture was filtered and the filtrate was evaporated under reduced pressure. The residue was purified by column chromatography over silica eluting with ethyl acetate:hexane (2:1) followed by recrystallisation from ethyl acetate/hexane to give the subtitle compound (0.062 g).

Melting point: 187–189° C. MS (EI) 360 (M$^+$). $^1$H NMR (CDCl$_3$) δ 1.85 (3H, s); 3.35 (3H, s); 4.62 (2H, s); 4.81 (1H, s); 4.95 (1H, s); 5.73 (2H, d); 7.55–7.43 (4H, m); 7.59 (1H, s); 7.85 (1H, d); 7.94–7.92 (2H, m).

(f) 3-[(3-Hydroxypropyl)thio]-5-methyl-7-(2-methyl-2-propenyl)-2-(1-naphthalenylmethyl)-2H-pyrazolo[3,4-d]pyrimidine-4,6[5H,7H]-dione A solution of lithium diisopropylamide (1.12 mmol) in tetrahydrofuran (6 ml) was added dropwise to a stirred solution of 5-methyl-7-(2-methyl-2-propenyl)-2-(1-naphthalenylmethyl)-2H-pyrazolo[3,4-d]pyrimidine-4,6 [5H,7H]-dione (0.20 g) and 3-{[dimethyl(1,1-dimethylethyl)silyl]oxy }propyl 4-methylphenylthiosulfonate (J. Med. Chem. 1995, 38, 2557) (0.262 g) in anhydrous tetrahydrofuran (20 ml) at −70° C. The solution was stirred for a further 1 hour at −70° C. and then allowed to warm to room temperature. Saturated aqueous sodium bicarbonate solution (10 ml) was added and the mixture was extracted with ethyl acetate. The organic extracts were dried over anhydrous magnesium sulfate, filtered and evaporated under reduced pressure. The residual oil was purified by column chromatography over silica eluting with acetone:hexane (1:5). The product was dissolved in acetonitrile (5 ml) and treated with 40% aqueous hydrofluoric acid (1 ml). After 5 minutes, the solution was neutralised with aqueous sodium bicarbonate solution and extracted with ethyl acetate. The organic extracts were washed with saturated aqueous sodium bicarbonate solution, dried over anhydrous magnesium sulfate, filtered and evaporated under reduced pressure. The residue was purified by column chromatography over silica eluting with acetone-:hexane (1:5 then 1:3) followed by recrystallisation from diethyl ether/hexane to give the title compound (0.11 g).

Melting point: 138–139° C. MS (FAB) 451 ((M+H)$^+$). $^1$H NMR (CDCl$_3$) δ 1.60 (3H, s); 1.75–1.80 (2H, m); 2.66 (1H, s, br); 3.29 (2H, t); 3.42 (3H, s); 3.72–3.78 (2H, m); 4.58 (2H, s); 4.83 (1H, s); 4.93 (1H, s); 5.98 (2H, s); 7.05 (1H, d); 7.42 (1H, t); 7.52–7.60 (2H, m); 7.85 (1H, d); 7.90 (1H, dd); 8.24 (1H, d).

EXAMPLE 2

5-Methyl-7-(2-methyl-2-propenyl)-2-(1-naphthalenylmethyl)-3-[(2-pyridinyl)thio]-2H-pyrazolo[3,4-d]pyrimidine-4,6[5H,7H]-dione

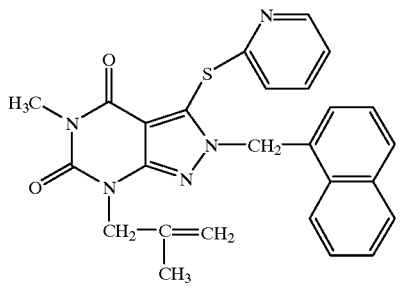

A solution of lithium diisopropylamide (2.24 mmol) in anhydrous tetrahydrofuran (10 ml) was added dropwise to a stirred solution of 5-methyl-7-(2-methyl-2-propenyl)-2-(1-naphthalenylmethyl)-2H-pyrazolo[3,4-d]pyrimidine-4,6 [5H,7H]-dione (Example 1(e), 0.20 g) and 2,2'-dipyridyl disulfide (0.246 g) in anhydrous tetrahydrofuran (15 ml) at −78° C. The solution was stirred for a further 0.5 hour at −78° C. and then allowed to warm to room temperature. Saturated aqueous sodium bicarbonate solution (10 ml) was added and the mixture was extracted with ethyl acetate. The organic extracts were dried over anhydrous magnesium sulfate, filtered and evaporated under reduced pressure. The residue was purified by column chromatography over silica eluting with diethyl ether:hexane (1:1 then 2:1) followed by recrystallisation from diethyl ether/hexane to give the title compound (0.08 g).

Melting point: 118–120° C. MS (FAB) 470 ((M+H)$^+$). $^1$H NMR (CDCl$_3$) δ 1.77 (3H, s); 3.34 (3H, s); 4.58 (2H, s); 4.82 (1H, s); 4.90 (1H, s); 5.96 (2H, s); 7.00–7.04 (2H, m); 7.15 (1H, d); 7.31 (1H, t); 7.38–7.55 (3H, m); 7.75 (1H, d); 7.81–7.84 (1H, m); 8.16–8.21 (1H, m); 8.28–8.32 (1H, m).

EXAMPLE 3

3-[(2-Hydroxyethyl)thio)-5-methyl-7-(2-methyl-2-propenyl)-2-(1-naphthalenylmethyl-2H-pyrazolo[3,4-d]pyrimidine-4,6[5H,7H]-dione

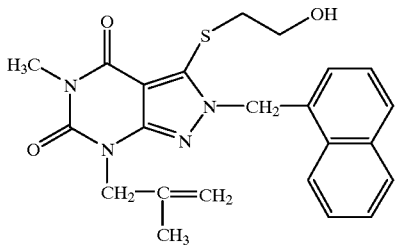

(a) Bis-2-{[dimethyl(1,1-dimethylethyl)silyl]oxy}ethyl disulfide

To a stirred solution of 2-hydroxyethyl disulfide (2 g) and imidazole (5.3 g) in dichloromethane (100 ml) was added dimethyl(1,1-dimethylethyl)silyl chloride (5.86 g). The solution was stirred overnight then diluted with diethyl ether, washed sequentially with dilute hydrochloric acid and aqueous sodium bicarbonate solution, dried over anhydrous magnesium sulfate, filtered and evaporated under reduced pressure. The residue was purified by column chromatography over silica eluting with hexane:diethyl ether (20:1) to give the subtitle compound as a clear oil (3.75 g).

MS (EI) 382 (M—CH$_3$)$^+$.

(b) 3-[(2-Hydroxyethyl)thio)-5-methyl-7-(2-methyl-2-propenyl)-2-(1-naphthalenylmethyl)-2H-pyrazolo[3,4-d]pyrimidine-4,6[5H,7H] -dione A solution of lithium diisopropylamide (3.36 mmol) in anhydrous tetrahydrofuran (25 ml) was added dropwise to a stirred solution of 5-methyl-7-(2-methyl-2-propenyl)-2-(1-naphthalenylmethyl)-2H-pyrazolo[3,4-d]pyrimidine-4,6 [5H,7H]-dione (Example 1(e), 0.30 g) and bis-2-{[dimethyl (1,1-dimethylethylsilyl]oxy}ethyl disulfide (0.642 g) in anhydrous tetrahydrofuran (30 ml) at −70° C. The solution was stirred for a further 0.5 hour at −78° C. and then allowed to warm to room temperature. Saturated aqueous sodium bicarbonate solution (10 ml) was added and the solution was extracted with ethyl acetate. The organic extracts were dried over anhydrous magnesium sulfate and evaporated under reduced pressure. The residue was purified by column chromatography over silica eluting with hexane:diethyl ether (2:1). The product was dissolved in acetonitrile (10 ml) and treated with 40% aqueous hydroflouric acid (1 ml). The solution was stirred overnight at room temperature then neutralised with aqueous sodium bicarbonate solution and extracted with ethyl acetate. The organic extracts were dried over anhydrous magnesium sulfate, filtered and evaporated under reduced pressure. The residue was purified by column chromatography over silica eluting with ethyl acetate to give the title compound (0.29 g) as a white solid.

Melting point: 135–137° C. MS (FAB) 437 ((M+H)$^+$) $^1$H NMR (CDCl$_3$) δ 1.78 (3H, s); 2.82 (2H, t); 3.42 (3H, s); 3.50–3.59 (2H, m); 3.79 (1H, t); 4.58 (2H, s); 4.81 (1H, s); 4.92 (1H, s); 6.02 (2H, s); 7.07(1H, d); 7.40 (1H, t); 7.52–7.60 (2H, m); 7.83 (1H, d); 7.90 (1H, d); 8.24 (1H, d).

EXAMPLE 4

3-(4-Hydroxybutyl)-5-methyl-7-(2-methylpropyl)-2-(1-naphthalenylmethyl)-2H-pyrazolo[3,4-d]pyrimidine-4,6(5H,7H)-dione

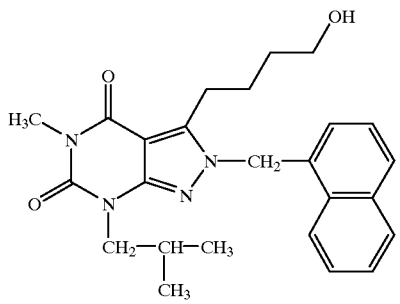

(a) 6-Chloro-3-methyl-1-(2-methylpropyl)pyrimidine-2,4[1H,3H]-dione

3-Iodo-2-methylpropane (3.0 ml) and potassium carbonate (3.5 g) were added to a solution of 6-chloro-3-methylpyrimidine-2,4[1H,3H]-dione (Example 1(b), 4.02 g) in dimethylformamide (50 ml). The mixture was heated at 90° C. for 24 hours then cooled to room temperature. The solution was diluted with hydrochloric acid (2.5 M) and extracted twice with diethyl ether. The combined organic extracts were dried over anhydrous magnesium sulfate, filtered and evaporated under reduced pressure. The residue was purified by column chromatography over silica eluting with iso-hexane:ethyl acetate (1:1) to give the subtitle compound (2.75 g) as a solid.

MS (ESI) 217/219 ((M+H)$^+$). $^1$H NMR (CDCl$_3$) δ 0.96 (6H, d); 2.10–2.22 (1H, m); 3.34 (3H, s); 3.90 (2H, d); 5.90 (1H, s).

(b) 6-Hydrazino-3-methyl-1-(2-methylpropyl)pyrimidine-2,4[1H,3H]-dione

Hydrazine hydrate (6.5 ml) was added to a solution of 6-chloro-3-methyl-1-(2-methylpropyl)pyrimidine-2,4[1H,3H]-dione (10.0 g) in ethanol (40 ml). The mixture was heated at reflux for 5 hours, cooled to room temperature and then evaporated under reduced pressure. The residue was recrystallised from ethanol to give the subtitle compound (8.8 g).

MS (APCI) 213 ((M+H)$^+$). $^1$H NMR (DMSO-d$_6$) δ 0.80 (6H, d); 1.92–2.07 (1H, m); 3.10 (3H, s); 3.70 (2H, d); 4.37 (2H, s, br); 5.11 (1H, s); 8.04 (1H, s, br).

(c) 1-Naphthaldehyde 3-methyl-1-(2-methylpropyl)-2,4[1H,3H]-dioxopyrimidine-6-hydrazone 6-Hydrazino-3-methyl-1-(2-methylpropyl)pyrimidine-2,4[1H,3H]-dione (2.5 g) was dissolved in warm methanol (100 ml) and treated with 1-naphthaldehyde (1.7 ml). After 1 hour, the precipitated solid was filtered and recrystallised from toluene to give the subtitle compound (1.34 g).

MS (APCI) 351 ((M+H)$^+$). $^1$H NMR (DMSO-d$_6$) δ 0.90 (6H, d); 2.03–2.19 (1H, m); 3.17 (3H, s); 3.92(2H, d); 5.78 (1H, s); 7.61 (2H, t); 7.70 (1H, t); 8.00 (1H, d) 8.04 (2H, d); 8.67 (1H, d); 9.07 (1H, s); 10.44 (1H, br s).

(d) 3-(4-Hydroxybutyl)—methyl-7-(2-methylpropyl)-2-(1-naphthalenylmethyl)-2H-pyrazolo[3,4-d]pyrimidine-4,6 (5H,7H)-dione 5-Hydroxypentanal (0.65 ml) was added to a solution of 1-naphthaldehyde 3-methyl-1-(2-methylpropyl)-2,4[1H,3H]-dioxopyrimidine-6-hydrazone(250 mg) in dimethylformamide (5 ml). The solution was heated at reflux for 14 hours, cooled to room temperature and evaporated under reduced pressure. The residue was dissolved in ethyl acetate and washed twice with dilute hydrochloric acid, twice with saturated aqueous sodium bicarbonate solution, and then with brine. The organic phase was dried over anhydrous magnesium sulfate, filtered and evaporated under reduced pressure. The residue was purified by column chromatography over silica eluting with iso-hexane:ethyl acetate (1:1) and then ethyl acetate to give the title compound (116 mg) as a foam.

MS (APCI) 435 ((M+H)$^+$) $^1$H NMR (DMSO-d$_6$) δ 0.85 (6H, d); 1.32–1.48 (4H, m); 2.12–2.26 (1H, m); 2.93 (2H, t); 3.20–3.30 (5H, m); 3.73 (2H, d); 4.31 (1H, t); 5.91 (2H, s); 6.90 (1H, d); 7.43 (1H, t); 7.58–7.62 (2H, m); 7.89 (1H, d); 7.97–8.00 (1H, m); 8.22–8.30 (1H, m).

EXAMPLE 5

5-Methyl-7-(2-methylpropyl)-2-(1-naphthalenylmethyl)-3-propylthio-2H-pyrazolo[3,4-d]pyrimidine-4,6(5H,7H)-dione

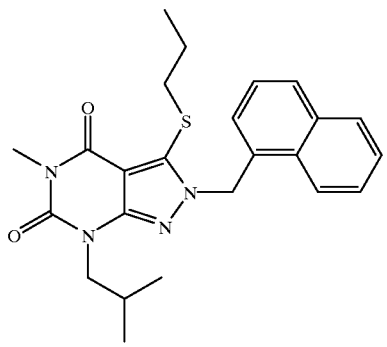

(a) 5-Methyl-7-(2-methylpropyl)-1H-pyrazolo[3,4-d]pyrimidine-4,6(5H,7H)-dione

In accordance with the teaching of German Patent No. 63,381, phosphorus oxychloride (4 ml) was added dropwise to an ice cooled solution of 6-hydrazino-3-methyl-1-(2-methylpropyl)pyrimidine-2,4[1H,3H]-dione (4.7 g) in dimethylformamide (15 ml). After 1 hour the reaction mixture was quenched by pouring onto water. The precipitated solid was collected by filtration, and dried in vacuo to give the subtitle compound (3.4 g).

Melting point: 200° C. MS (−ve APCI) ((M−H)$^−$) 221 $^1$H NMR (DMSO-d$_6$) δ 0.87 (6H, d), 2.22 (1H, m), 3.22 (3H, s), 3.77 (2H, d), 8.47 (I H, brs), 13.46 (1H, brs).

(b) 5-Methyl-7-(2-methylpropyl)-2-(1-naphthalenylmethyl)-2H-pyrazolo[3,4-d]pyrimidine-4,6 (5H,7H)-dione In accordance with the teaching of German Patent No. 63,381, 1-(chloromethyl)-naphthalene (2.2 g), potassium carbonate (1.6 g) and 5-methyl-7-(2-methylpropyl)-2H-pyrazolo[3,4-d]pyrimidine-4,6(5H,7H)-dione (2.5 g) were combined in acetone (40 ml) and heated under reflux for 3 hours and then cooled to ambient temperature. Water (200 ml) was added and the precipitated solid was collected by filtration. The solid was triturated with isohexane and then dried in vacuo to give the title compound (3.64 g).

Melting point: 178° C. MS (+ve APCI) ((M+H)$^+$) 363 $^1$H NMR (DMSO-d$_6$) δ 0.83 (6H, d), 2.14 (1H, m), 3.19 (3H, s), 3.72 (2H, d), 5.88 (2H, s), 7.28 (1H, d), 7.48 (1H, t), 7.55–7.65 (2H, m), 7.93 (1H, d), 8.00 (1H, d), 8.22 (1H,d), 8.55 (1H, s).

(c) 5-Methyl-7-(2-methylpropyl)-2-(1-naphthalenylmethyl)-3-propylthio-2H-pyrazolo[3,4-d]pyrimidine-4,6(5H,7H)-dione N-butyl lithium (1.5 M, 1.4 ml) was added to a solution of 5-methyl-7-(2-methylpropyl)-2-(1-naphthalenylmethyl)-2H-pyrazolo[3,4-d]pyrimidine-4,6(5H,7H)-dione (200 mg) and dipropyl disulfide (0.175 ml) in tetrahydrofuran (10 ml) cooled to −78° C. After 1 hour the reaction mixture was warmed to ambient temperature and after a further hour the reaction was quenched with water. The reaction mixture was diluted with ether and washed thrice with 2 M sodium hydroxide solution and once with brine. The organic phase was dried over magnesium sulfate, concentrated in vacuo and purified by chromatography on silica gel (isohexane:ethyl acetate 9:1–4:1), followed by recrystallisation from isohexane to give the title compound (24 mg).

Melting point: 105° C. MS (+ve APCI) ((M+H)⁺) 437 ¹H NMR (DMSO d₆) δ 0.8–0.9 (9H, m), 1.4–1.5 (2H, m), 2.17 (1H, m), 3.16 (2H, t), 3.23 (3H, s), 3.72 (2H, d), 5.99 (2H, s), 6.89 (1H, d), 7.43 (1H, t), 7.55–7.65 (2H, m), 7.89 (1H, d), 7.98 (1H, d), 8.30 (1H,d).

EXAMPLE 6

3-[(3-Hydroxypropyl)thio]-5-methyl-7-(2-methylpropyl)-2-(1-naphthalenylmethyl)-2H-pyrazolo[3,4-d]pyrimidine-4,6(5H,7H)-dione

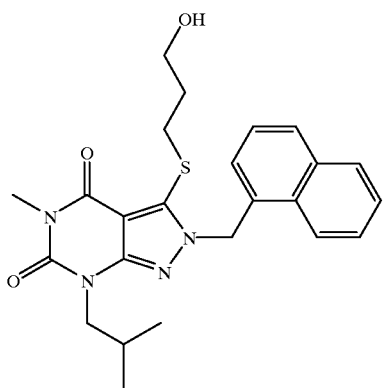

Lithium diisopropylamide (3.3 mmol) was added to a solution of 5-methyl-7-(2-methylpropyl)-2-(1-naphthalenylmethyl)-2H-pyrazolo[3,4-d]pyrimidine-4,6 (5H,7H)dione (600 mg) and 3-{[dimethyl(1,1-dimethylethyl)silyl]oxy }propyl 4-methylphenylthiosulfonate (J. Med. Chem. 1995, 38, 2557) (720 mg) in tetrahydrofuran (20 ml) cooled to −78° C. After 2 hours the reaction mixture was warmed to ambient temperature and after a further hour quenched with water. The reaction mixture was diluted with ethyl acetate and was washed twice with dilute hydrochloric acid, twice with saturated sodium hydrogen carbonate solution, once with brine, and then dried over magnesium sulfate, filtered and concentrated. The residue was dissolved in tetrahydrofuran (20 ml) and tetrabutylammonium fluoride (1 M in tetrahydrofuran, 2 ml) was added. After 18 hours the reaction mixture was quenched with saturated sodium hydrogen carbonate solution and extracted with ether. The ether extract was washed once with water and once with brine, then dried over magnesium sulfate, filtered and concentrated. Chromatography of the residue on silica gel (isohexane:ethyl acetate 1:1–1:2) followed by preparative reverse phase HPLC and recrystallisation from isohexane : ethyl acetate gave the title compound (156 mg).

Melting point: 135° C. MS (+ve APCI) ((M+H)⁺) 453 ¹H NMR (DMSO d₆) δ 0.83 (6H, d), 1.5–1.6 (2H, m), 2.19 (1H, m), 3.23 (3H, s; 2H, t), 3.32 (2H, q), 3.73 (2H, d), 4.48 (1H, t), 5.99 (2H, s), 6.89 (1H, d), 7.43 (1H, t), 7.55–7.65 (2H, m), 7.89 (1H, d), 7.98 (1H, dd), 8.30 (1H,dd).

EXAMPLE 7

Methyl 4-[(4,5,6,7-tetrahydro-5-methyl-7-{2-methylpropyl}-2-{1-naphthalenyl-methyl}-4,6-dioxo-2H-pyrazolo[3,4-d]pyrimidin-3-yl)thio]butanoic Acid

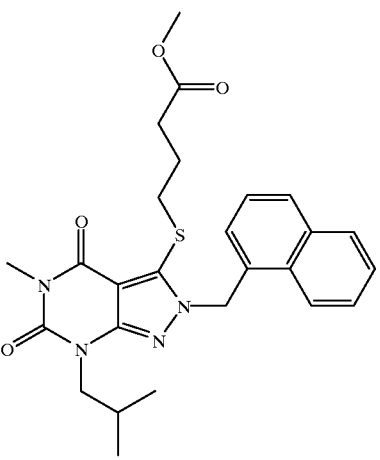

(a) 4,4,4-Trimethoxybutyl para-toluenethiosulfonate

A mixture of para-toluenethiosulfonic acid potassium salt (24 mmol), trimethyl 4-bromoorthobutyrate (22 mmol) and hexamethylphosphoramide (30 ml) was stirred at room temperature for 48 hours and then poured into 10:1 hexane/diethyl ether (500 ml). The mixture was shaken vigorously, then washed with water (2×200 ml) and then with brine. The organic phase was dried over magnesium sulfate and evaporated to dryness in vacuo to give the subtitle ester as an oil (5.3 g).

¹H NMR (CDCl₃) δ 1.95(2H, m), 2.37(2H, t), 2.44(3H, s), 3.02(2H, t), 3.16(9H, s), 7.33(2H, d), 7.80(2H, d).

(b) Methyl 4-[(4,5,6,7-tetrahydro-5-methyl-7-{2-methylpropyl}-2-{1-naphthalenylmethyl}-4,6-dioxo-2H-pyrazolo[3,4-d]pyrimidin-3-yl)thio]butanoate Lithium diisopropylamide (2.8 mmol) was added to a solution of 5-methyl-7-(2-methylpropyl)-2-(1-naphthalenylmethyl)-2H-pyrazolo[3,4-d]pyrimidine-4,6 (5H,7H)-dione (500 mg) in tetrahydrofuran (20 ml) cooled to −78° C. After 10 minutes 4,4,4-trimethoxybutyl para-toluenethiosulfonate (1.2 g) was added to the reaction. After 2 hours the reaction mixture was warmed to ambient temperature and after a further hour quenched with dilute hydrochloric acid. The reaction mixture was diluted with ethyl acetate and washed twice with dilute hydrochloric acid, twice with saturated sodium hydrogen carbonate solution, once with brine and then dried over magnesium sulfate. The organic phase was concentrated in vacuo and the residue was chromatographed on silica gel (isohexane:ethyl acetate 3:1–2:1) and then triturated with isohexane to give the title compound (340 mg).

Melting point: 100° C. MS (+ve APCI) 495 ((M+H)⁺) ¹H NMR (DMSO d₆) δ 0.84 (6H, d), 1.65 (2H, quint), 2.19 (1H, m), 2.28 (2H, t), 3.20–3.25 (5H, m), 3.52 (3H, s), 3.74 (2H, d), 5.99 (2H, s), 6.89 (1H, d), 7.43 (1H, t), 7.55–7.65 (2H, m), 7.89 (1H, d), 8.00 (1H, dd), 8.30 (1H,dd).

EXAMPLE 8

4-[(4,5,6,7-tetrahydro-5-methyl-7-{2-methylpropyl}-2-{1-naphthalenylmethyl}-4,6-dioxo-2H-pyrazolo[3,4-d]pyrimidin-3-yl)thio]butanoic Acid

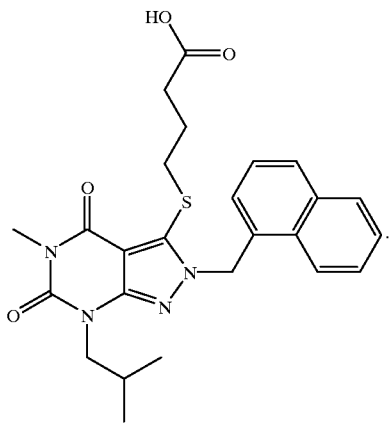

Lithium hydroxide monohydrate (80 mg) was added to a solution of methyl 4-[(4,5,6,7-tetrahydro-5-methyl-7-{2-methylpropyl}-2-{1-naphthalenylmethyl}-4,6-dioxo-2H-pyrazolo[3,4-d]pyrimidin-3-yl)thio]butanoic acid (250 mg) in tetrahydrofuran (20 ml) and water was then added to give a homogeneous solution. After 18 hours the reaction mixture was partitioned between ether and 2 M sodium hydroxide. The aqueous phase was acidified with concentrated hydrochloric acid and extracted with ethyl acetate which was then dried over magnesium sulfate. The organic phase was concentrated in vacuo and recrystallised from cyclohexane-:ethyl acetate to give the title compound (130 mg).

Melting point: 149° C. MS (+ve APCI) 481 ((M+H)$^+$) $^1$H NMR (DMSO d$_6$) δ 0.84 (6H, d), 1.65 (2H, quint), 2.10–2.25 (3H, m), 3.20–3.25 (5H, m), 3.74 (2H, d), 5.99 (2H, s), 6.90 (1H, d), 7.45 (1H, t), 7.55–7.65 (2H, m), 7.89 (1H, d), 7.98 (1H, dd), 8.29 (1H,dd).

EXAMPLE 9

3-[(3-Hydroxypropyl)thio]-5-methyl-7-(2-methylpropyl)-2-(2-{phenylsulfonylmethyl}phenylmethyl)-2H-pyrazolo[3,4-d]pyrimidine-4,6(5H,7H)-dione

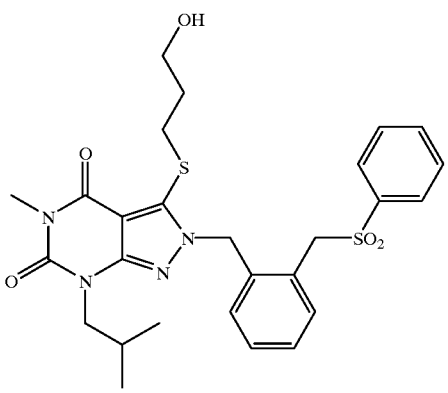

(a) 3-[(3-Hydroxypropyl)thio]-5-methyl -(2-methylpropyl)-1H-pyrazolo[3,4-d]pyrimidine-4,6(5H,7H1)-dione Lithium diisopropylamide (10.7 mmol) was added to a solution of 2-(4-methoxyphenylmethyl-5-methyl-7-(2-methylpropyl)2H-pyrazolo[3,4-d]pyrimidine-4,6(5H,7H)-dione (1.83 g) and 3-{[dimethyl(1,1-dimethylethyl)silyl]oxy}propyl 4-methylphenylthiosulfonate (J. Med. Chem. 1995, 38, 2557) (3.0 g) in tetrahydrofuran (30 ml) at −78° C. After 1.5 hours the reaction mixture was warmed to ambient temperature and after a further 2 hours water was added. The reaction mixture was diluted with ethyl acetate and washed twice with dilute hydrochloric acid, twice with saturated sodium hydrogen carbonate solution, once with brine and then dried over magnesium sulfate and concentrated in vacuo. The residue was dissolved in trifluoroacetic acid (10 ml) and heated to 100° C. for 4 hours. The mixture was allowed to cool and was then evaporated under reduced pressure. The residue was dissolved in methanol (30 ml), saturated sodium hydrogen carbonate (1.1 g) was added, and the mixture was stirred at room temperature for 1 hour and then evaporated under reduced pressure. The resultant residue was dissolved in ethyl acetate and washed once with saturated sodium hydrogen carbonate solution, twice with brine, then dried over magnesium sulfate and concentrated in vacuo. Chromatography on silica gel (isohexane:ethyl acetate 1:2) gave the title compound (1.0 g).

Melting point: 103–9° C. MS (+ve APCI) 313 ((M+H)$^+$) $^1$H NMR (DMSO d$_6$) δ 0.87 (6H, d), 1.70 (2H, vbrs), 2.20 (1H, vbrs), 3.18 (5H, s), 3.47 (2H, t), 3.70 (2H, d).

(b) 3-[(3-Hydroxypropyl)thio]-5-methyl-7-(2-methylpropyl)-2-(2-{phenylsulfonylmethyl}phenylmethyl)-2H-pyrazolo[3,4-d]pyrimidine-4,6(5H,7H)-dione 3-[(3-Hydroxypropyl)thio]-5-methyl-7-(2-methylpropyl)-1H-pyrazolo[3,4-d]-pyrimidine-4,6(5H,7H)-dione (94 mg), potassium carbonate (90 mg) and 2-(phenylsulfonylmethyl)benzyl bromide (105 mg) were combined in dimethylsulfoxide (11 ml). After 5 hours at room temperature the reaction mixture was diluted with ethyl acetate and washed thrice with water, twice with dilute hydrochloric acid, once with brine, then dried over magnesium sulfate and then concentrated in vacuo. Chromatography on silica gel (isohexane:isopropanol 4:1) gave the title compound (70 mg).

Melting point: 50° C. (foam) MS (+ve APCI) 557 ((M+H)$^+$) $^1$H NMR (DMSO d$_6$) δ 0.81 (6H, d), 1.54 (2H, quint), 2.12 (1H, m), 3.19 (2H, t), 3.22 (3H, s), 3.37 (2H,q), 3.68 (2H, d), 4.48 (1H, t), 5.00 (2H, s), 5.61 (2H, s), 6.70 (1H,d), 7.13 (1H, d), 7.2–7.3 (2H, m), 7.65 (2H, t), 7.78 (1H, t), 7.82 (2H, d).

The following compounds were prepared following the method of Example 9(b) using 3-[(3-hydroxypropyl)thio]-5-methyl-7-(2-methylpropyl)-1H-pyrazolo[3,4-d]pyrimidine-4,6(5H,7H)-dione and the appropriate halide.

| Example | | Name | Mtg. Pt. | MS | ¹H NMR |
|---|---|---|---|---|---|
| 10 | 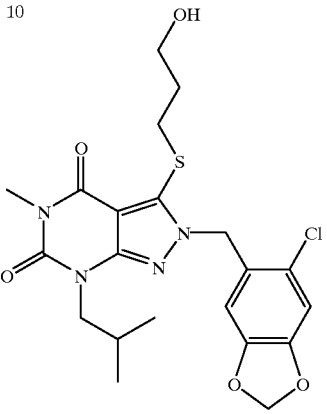 | 2-({5-Chlorobenzo[1,3]dioxol-6-yl}methyl)-3-[3-hydroxy-propyl)thio]-5-methyl-7-(2-methylpropyl)-2H-pyrazolo[3,4-d]pyrimidine-4,6(5H,7H)-dione | 144° C. | | (CDCl₃)δ 0.93(6H, d), 1.80(2H, quint), 2.30(1H, m), 2.60(1H, brt), 3.30(2H, t), 3.40(3H, s), 3.80(2H, brq), 3.85(2H, d), 5.50(2H, s), 6.00(2H, s), 6.30(1H, s), 6.90(1H, s). |
| 11 | 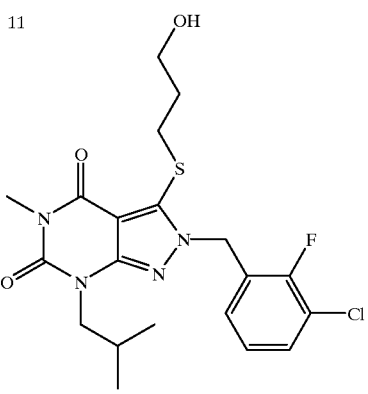 | 2-(3-Chloro-2-fluorophenyl-methyl)-3-[(3-hydroxypropyl)-thio]-5-methyl-7-(2-methyl-propyl)-2H-pyrazolo[3,4-d]pyrimidine-4,6(5H,7H)-dione | 76–9° C. | 455/ 457 | (CDCl₃)δ 0.90(6H, d), 1.84(2H, quint), 2.22(1H, m), 2.65(1H, brt), 3.18(2H, t), 3.40(3H, s), 3.62(2H, brq), 4.00(2H, d), 5.55(2H, s), 6.86(1H, dt), 7.02(1H, dt), 7.33(1H, dt). |
| 12 | 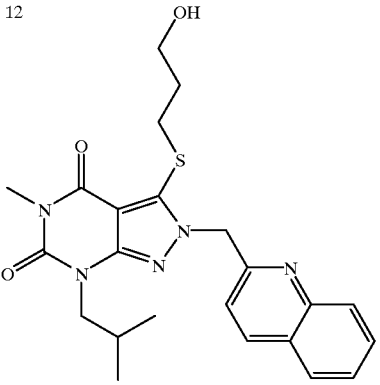 | 3-[(3-Hydroxypropyl)-thio]-5-methyl-7-(2-methyl-propyl)-2-(2-quinolinylmethyl)-2H-pyrazolo[3,4-d]pyrimidine-4,6(5H,7H)-dione | 131° C. | 454 | (DMSO-d₆)δ 0.83(6H, d), 1.60(2H, quint), 2.21(1H, m), 3.20(2H, t), 3.24(3H, s), 3.30 (2H, q), 3.72(2H, d), 4.54(1H, t), 5.80(2H, s), 7.28(1H, d), 7.60(1H, dt), 7.74(1H, dt), 7.88(1H, d), 8.00(1H, d), 8.37(1H, d). |

Pharmacological data

EXAMPLE 13

Inhibition of Human Mixed Lymphocyte Reaction (MLR)

The MLR test was performed in 96well flat bottomed microtitre plates. Compounds were prepared as 10 mM stock solution in dimethyl sulphoxide. A 50 fold dilution of this was prepared in RPMI. Serial dilutions were prepared from this solution. 10 μl of the 50 fold diluted stock, or dilutions of it, were added to the well to give concentrations in the assay starting at 9.5 μm and going down. Into each well was placed 1.5×10⁵ cells from each of two responding donors in a final volume of 0.2 ml RPMI 1640 medium supplemented with 10% human serum, 2 mM L-glutamine and penicillin/streptomycin. The cells were incubated at 37° C. in a humidified atmosphere at 5% carbon dioxide for 120 hours. ³H-Thymidine (0.5 μCi) was added for the final 6 hours of the incubation. The level of radioactivity incorporated by the cells was then determined, which is a measure of T-cell proliferation.

The title compounds of Examples 1 to 12 were found to exhibit an $IA_{50}$ value of less than $1×10^6$ M in the above test.

We claim:

1. A compound of formula (I):

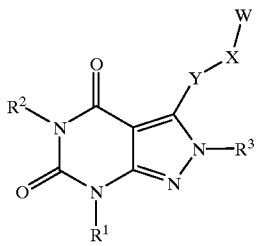

in which:
R$^1$ is C$_{1-6}$alkyl, C$_{3-6}$alkenyl or C$_{3-6}$cycloalkyl;
R$^2$ is C$_{1-4}$alkyl or C$_{3-6}$alkenyl;
R$^3$ is 1- or 2-indanyl, 1- or 2-(1,2,3,4-tetrahydronaphthalenyl), 9-fluorenyl, acenaphthyl or CHR$^4$(CH$_2$)$_n$Ar where n is 0 or 1, R$^4$ is hydrogen or C$_{1-6}$alkyl and Ar is quinolinyl, naphthalenyl, benzodioxolinyl optionally susbstituted by one or more halogen atoms, or phenyl optionally substituted by one or more substituent groups selected from halogen, C$_{1-6}$alkyl, C$_{1-6}$alkoxy and phenylsulfonylmethyl;
W is H, CH$_2$OH, CO$_2$H, CO$_2$C$_{1-6}$alkyl, CH$_2$NR$^5$R$^6$, CONR$^5$R$^6$, where R$^5$ and R$^6$ are independently hydrogen or C$_{1-6}$alkyl, or W is pyridyl or phenyl, each of which may be optionally substituted by one or more substituent groups selected from halogen, hydroxyl, C$_{1-6}$alkyl and C$_{1-6}$alkoxy;
X is a bond or C$_{1-5}$alkylene;
Y is S$_p$, C≡C, CH=CH, CH$_2$CH$_2$ or CH$_2$CH=CH; and or a pharmaceutically acceptable salt thereof, provided that:
X is not a bond when W is H, CH$_2$OH, CO$_2$H, CO$_2$C$_{1-6}$alkyl, CH$_2$NR$^5$R$^6$ or CONR$^5$R$^6$ and Y is sulfur.

2. A compound according to claim 1, wherein R$^1$ is C$_{1-4}$alkyl or C$_{3-4}$alkenyl.

3. A compound according to claim 1, wherein R$^2$ is C$_{1-4}$alkyl.

4. A compound according to claim 1, wherein R$^3$ is CHR$^4$(CH$_2$)$_n$Ar in which n is 0, R$^4$ is hydrogen and Ar is quinolinyl, naphthalenyl, benzodioxolinyl substituted by one or more halogen atoms, or phenyl substituted by one or more substituent groups selected from halogen atoms and phenylsulfonylmethyl.

5. A compound according to claim 1, wherein Y is sulfur or CH$_2$CH$_2$.

6. A compound according to claim 1, wherein X is C$_{1-3}$alkylene.

7. A compound according to claim 1, wherein W is H, CH$_2$OH, CO$_2$H, CO$_2$C$_{1-6}$alkyl or pyridyl.

8. A compound according to claim 1 which is:
3-[(3-Hydroxypropyl)thio]-5-methyl-7-(2-methyl-2-propenyl)-2-(1-naphthalenylmethyl)-2H-pyrazolo[3,4-d]pyrimidine-4,6[5H,7H]-dione, or
5-Methyl-7-(2-methyl-2-propenyl)-2-(1-naphthalenylmethyl)-3-[(2-pyridinyl)thio]-2H-pyrazolo[3,4-d]pyrimidine-4,6[5H,7H]-dione, or
3-[(2-Hydroxyethyl)thio)-5-methyl-7-(2-methyl-2-propenyl)-2-(1-naphthalenylmethyl-2H-pyrazolo[3,4-d]pyrimidine-4,6[5H,7H]-dione, or
3-(4-Hydroxybutyl)-5-methyl-7-(2-methylpropyl)-2-(1-naphthalenylmethyl)-2H-pyrazolo[3,4-d]pyrimidine-4,6(5H,7H)-dione, or
5-Methyl-7-(2-methylpropyl)-2-(1-naphthalenylmethyl)-3-propylthio-2H-pyrazolo[3,4-d]pyrimidine-4,6(5H,7H)-dione, or
3-[(3-Hydroxypropyl)thio]-5-methyl-7-(2-methylpropyl)-2-(1-naphthalenylmethyl)-2H-pyrazolo[3,4-d]pyrimidine-4,6(5H,7H)-dione, or
Methyl 4-[(4,5,6,7-tetrahydro-5-methyl-7-{2-methylpropyl}-2-{1-naphthalenylmethyl}-4,6-dioxo-2H-pyrazolo[3,4-d]pyrimidin-3-ylthio]butanoic acid, or
4-[(4,5,6,7-tetrahydro-5-methyl-7-{2-methylpropyl}-2-{1-naphthalenylmethyl}-4,6-dioxo-2H-pyrazolo[3,4-d]pyrimidin-3-yl)thio]butanoic acid, or
3-[(3-Hydroxypropyl)thio]-5-methyl-7-(2-methylpropyl)-2-(2-{phenylsulfonylmethyl}phenylmethyl)-2H-pyrazolo[3,4-d]pyrimidine-4,6(5H,7H)-dione, or
2-({5-Chlorobenzo[1,3]dioxol-6-yl}methyl)-3-[(3-hydroxypropyl)thio]-5-methyl-7-(2-methylpropyl)-2H-pyrazolo[3,4-d]pyrimidine-4,6(5H,7H)dione, or
2-(3-Chloro-2-fluorophenylmethyl)-3-[(3-hydroxypropylthio]-5-methyl-7-(2-methylpropyl)-2H-pyrazolo[3,4-d]pyrimidine-4,6(5H,7H)-dione, or
3-[(3-Hydroxypropyl)thio]-5-methyl-7-(2-methylpropyl)-2-(2-quinolinylmethyl)-2H-pyrazolo[3,4-d]pyrimidine-4,6(5H,7H)dione, or
a pharmaceutically acceptable salt of any one thereof.

9. A process for the preparation of a compound of formula (I) as defined in claim 1 which comprises
(a) reaction of a compound of formula (II):

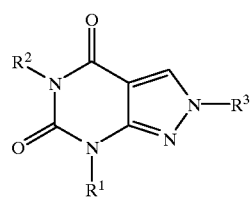

in which R$^1$, R$^2$ and R$^3$ are as defined in formula (I) with a compound of formula (III):

L—Y—X—W     (III)

in which L is a leaving group, Y is sulphur, and X and W are as defined in formula (I), or (b) when Y is CH$_2$CH$_2$ or CH$_2$CH=CH and R$^3$ is CHR$^4$(CH$_2$)$_n$Ar, reaction of a compound of formula (IV):

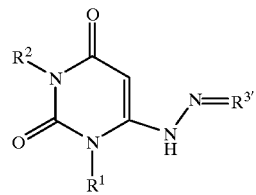

in which R$^{3'}$ is a precursor to the R$^3$ group CHR$^4$(CH$_2$)$_n$Ar and R$^1$ and R$^2$ are as defined in formula (I), with a compound of formula (V):

OHC—Y—X—W     (V)

in which Y is CH$_2$CH, or CH$_2$CH=CH and W and X are as defined in formula (I), or (c) when Y is C≡C, CH=CH or CH$_2$CH=CH, reacting a compound of formula (VI):

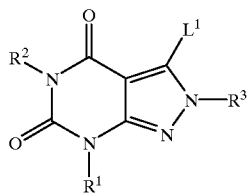
(VI)

in which L$^1$ represents a leaving group and R$^1$, R$^2$ and R$^3$ are as defined in formula (I) with a compound of formula (VII) or (VIII):

H$_2$C=CH—X$^a$W      (VII)

HC≡C—XW      (VIII)

wherein, in formula (VII), X$^a$ is a bond or C$_{1-6}$alkylene and W is as defined in formula (I), and wherein, in formula (VIII), W and X are as defined in formula (I), and optionally thereafter:

converting the compound of formula (I) hydrogenation of 4 groups to another compound of formula (I), and/or forming a pharmaceutically acceptable salt.

10. A pharmaceutical composition comprising a compound of formula (I), or a pharmaceutically acceptable salt thereof, as claimed in claim 1 in combination with a pharmaceutically acceptable diluent or carrier.

11. A process for the preparation of a pharmaceutical composition which comprises mixing a compound of formula (I), or a pharmaceutically acceptable salt thereof, as defined in claim 1 with a pharmaceutically acceptable diluent or carrier.

12. A method of treating allograft rejection, which comprises administering to a patient a therapeutically effective amount of a compound of formula (I) or a pharmaceutically acceptable salt thereof, as claimed in claim 1.

\* \* \* \* \*